United States Patent [19]

Tsuboi et al.

[11] Patent Number: 5,683,686
[45] Date of Patent: Nov. 4, 1997

[54] ANTI-FOULING COMPOSITIONS COMPRISING N-PHENYLISOTHIAZALONE DERIVATIVES AND FOULING CONTROL OF HARMFUL AQUATIC ORGANISMS USING SAME

[75] Inventors: Makoto Tsuboi; Shuhei Yuki, both of Hiroshima; Akiko Kakimizu, Nishinomiya; Kenji Arai, Toyonaka; Masato Mizutani, Nishimomiya, all of Japan

[73] Assignees: Chugoku Marine Paints, Ltd., Hiroshima-ken; Sumitomo Chemical Company, Limited, Osaka-fu, both of Japan

[21] Appl. No.: 364,465

[22] Filed: Dec. 27, 1994

[30] Foreign Application Priority Data

Dec. 27, 1993 [JP] Japan .................... 5-333791

[51] Int. Cl.⁶ .................... C07D 5/16; C07D 275/02
[52] U.S. Cl. .................... 124/78.09; 514/372; 548/214
[58] Field of Search .................... 424/78.09; 514/372; 548/214

[56] References Cited

U.S. PATENT DOCUMENTS 4,127,687  11/1978  Dupont.
5,552,423  9/1996  Kakimizu et al. .................... 514/372

FOREIGN PATENT DOCUMENTS 0490565  6/1992  European Pat. Off..
4146213  5/1992  Japan .................... 424/78.09
2277742  11/1994  United Kingdom.

*Primary Examiner*—Peter F. Kulkosky
*Attorney, Agent, or Firm*—Birch, Stewart, Kolasch & Birch, LLP

[57] ABSTRACT

There are disclosed a controlling agent and an antifouling composition against harmful aquatic organisms, which include a particular N-phenylisothiazolone derivative of the formula:

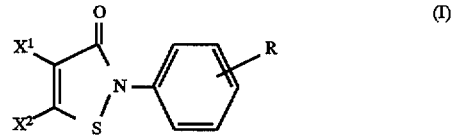

wherein $X^1$ and $X^2$ are the same or different and are independently hydrogen, chlorine or bromine; and R is haloalkoxy. Also disclosed is a method for preventing or inhibiting the adhesion of harmful aquatic organisms to water-exposed articles, which includes applying the antifouling composition to the water-exposed articles.

23 Claims, No Drawings

ANTI-FOULING COMPOSITIONS COMPRISING N-PHENYLISOTHIAZALONE DERIVATIVES AND FOULING CONTROL OF HARMFUL AQUATIC ORGANISMS USING SAME

FIELD OF THE INVENTION

The present invention relates to fouling control of harmful aquatic organisms which adhere to various water-exposed articles. The term "water-exposed articles" is used herein to cover marine vessels, buoys, littoral industrial plants, inlet channels for cooling water in thermal or nuclear power stations, drilling rigs for submarine oil fields, harbor facilities and sea pollution preventive bands for ocean civil engineering works, and the like,

BACKGROUND OF THE INVENTION

As there can be found many kinds of animals and plants living in the sea, various organisms may often adhere to water-exposed articles and have adverse effects thereon. The adhesion of such harmful aquatic organisms will cause a decrease in the service speed and an increase in the fuel consumption of marine vessels, and a decrease in the carrying capacity of inlet channels of cooling water.

To control these adhering organisms, various antifouling agents such as cuprous oxide and some isothiazolone derivatives disclosed in U.S. Pat. No. 4,127,687 have hitherto been known; however, their efficacy is not sufficient.

SUMMARY OF THE INVENTION

Under these circumstances, the present inventors have intensively studied to find methods of more effectively preventing and inhibiting various organisms adhering to water-exposed articles. As a result, they found that particular N-phenylisothiazolone derivatives have an effect on the prevention and inhibition of adhesion of harmful aquatic organisms, for example, harmful aquatic animals such as barnacles and sea mussels; harmful aquatic plants such as algae and diatoms; and harmful aquatic objects such as slime, thereby completing the present invention.

Thus, the present invention provides a controlling agent and an antifouling composition against harmful aquatic organisms, which comprise an N-phenylisothiazolone derivative of the formula:

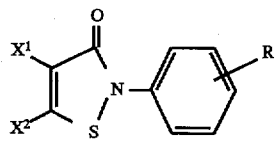

wherein $X^1$ and $X^2$ are the same or different and are independently hydrogen, chlorine or bromine; and R is haloalkoxy.

The present invention also provides a method for preventing and inhibiting the adhesion of harmful aquatic organisms to water-exposed articles, which comprises applying an effective amount of the antifouling composition of the present invention to the water-exposed articles.

DETAILED DESCRIPTION OF THE INVENTION

The controlling agent and antifouling composition of the present invention contain an N-phenylisothiazolone derivative of the formula (I), which is hereinafter referred to as the compound (I), as an active ingredient.

In the compound (I), the substituent R is haloalkoxy, usually $C_1$–$C_8$ haloalkoxy, and preferably $C_1$–$C_4$ haloalkoxy. Typical examples of the haloalkoxy are fluoroalkoxy such as difluoromethoxy, trifluoromethoxy, chlorodifluoromethoxy, pentafluoroethoxy and 1,1,2,2-tetrafluoroethoxy.

The compound (I) has an effect on the prevention and inhibition of harmful aquatic organisms adhering to water-exposed articles, and such an effect can be retained for a long period of time. Examples of the harmful aquatic organisms are aquatic animals such as barnacles (Balanornorpha), Serpula, polyzoans (Polyzoa), Ascidiacea, Hydrozoa and mollusks (Mollusca); aquatic plants such as Ulva, Enteromorpha, Ectocarpus and diatoms (Diatomaceae); and slime.

In case where the compound (I) is used for the purpose of preventing and inhibiting the adhesion and propagation of harmful aquatic organisms adhering to water-exposed articles, it may be applied in the form or a solution or emulsion. Preferably, it is applied in the form of a resin-containing composition. In particular, to water-exposed articles present in the sea, the antifouling composition of the present invention is applied.

The compound (I) can be made into an antifouling composition by ordinary formulation which is usually employed in the field of paints. It is noted that the compound (I) has no adverse effect on the storage stability, such as viscosity increase and quality change.

The antifouling composition of the present invention contains the compound (I) in admixture with a resin. Examples of the resin are vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin. Preferred are vinyl chloride resins, vinyl chloride-vinyl acetate copolymers, vinyl chloride-vinyl isobutyl ether copolymers, acrylic resins and styrene-butadiene copolymers.

The resin is mixed in an amount of 0.1% to 80% by weight, preferably 0.1% to 60% by weight, based on the total weight of the antifouling composition of the present invention.

The antifouling composition of the present invention may further contain various additives which are usually used in conventional paints, for example, plasticizers such as chlorinated paraffin and trimetacresyl phosphate; color pigments such as red iron oxide and titanium dioxide; extender pigments such as zinc oxide and silica powder; and organic solvents such as xylene and methyl isobutyl ketone.

Preferably, a copper compound or a metallic copper is added to the controlling agent and antifouling composition of the present invention to obtain more excellent controlling effects. Examples of the copper compound are cuprous oxide, copper rhodanide, oxine-copper, copper naphthenate, copper glycinate, cuprous chloride and cuprous carbonate. Preferred are cuprous oxide and copper rhodanide.

The controlling agent and the antifouling composition of the present invention may further contain other conventional antifouling agents, if required. Examples of the antifouling agent are those which have been found in the 209th research meeting of the Japan Shipbuilding Research Association, such as zinc dimethyldithiocarbamate, 2-methylthio-4-t-butylamino-6-cyclopropylamino-s-triazine, 2,4,5,6- tetrachloroisophthalonitrile, N,N-dimethyl-N'-(3,4-dichlorophenyl)urea, 4,5-dichloro-2-n-octyl-4-isothiazolin-3-one, N-(fluorodichloromethylthio)phthalimide, N,N-dimethyl-N'-phenyl-N'-(fluorodichloromethylthio) sulfamide, 2-pyridinethiol-1-oxide zinc salt, tetramethylthiuram disulfide, Cu-10% Ni solid solution alloy, N-(2,4,6-trichlorophenyl)maleimide, 2,3,5,6-tetrachloro-4-(methylsulfonyl)pyridine, 3-iodo-2-propynylbutylcarbamate, diiodomethyl-p-tolylsulfone, bis-dimethyldithiocarbamoyl zinc ethylenebisdithiocarbamate and tetraphenylborane pyridine salt.

The compound (I) is mixed in an amount of 0.1 to 60% by weight, preferably 0.1 to 40% by weight, based on the total weight of the controlling agent or the antifouling composition of the present invention. When the amount is less than 0.1% by weight, no controlling effect will be expected. When the amount is geater than 60% by weight, defects such as cracks and peeling will readily occur on the coating film formed from the antifouling composition.

In case where a copper compound or a metallic copper is to be added to the controlling agent or the antifouling composition of the present invention, the proportion of the copper compound or the metallic copper to the compound (I) may vary case by case, but it is preferably in the range of 0.1 to 100 parts by weight to one part by weight of the compound (I). The total amount of compound (I) and copper compound or metallic copper is preferably 0.1% to 80% by weight, based on the total weight of the controlling agent or the antifouling composition of the present invention. When the total amount is less than 0.1% by weight, no controlling effect will be expected. When the total amount is greater than 80% by weight, defects such as cracks and peeling will readily occur on the coating film formed from the antifouling composition, which makes it difficult to attain the desired antifouling effect.

The compound (I) wherein $X^1$ is hydrogen can be prepared by reacting a disulfide of the formula (II):

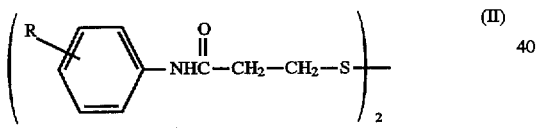

wherein R is as defined above, with a halogenacing agent. The compound (I) wherein $X^1$ is chlorine or bromine can be prepared by reacting the compound (I) wherein $X^1$ is hydrogen, with a halogenacing agent.

The above reaction is usually carried out in the presence or absence of a solvent at a temperature of 0° to 150° C. for a period of 1 to 24 hours. The halogenacing agent is used in an amount of 1 to 10 equivalents to one equivalent of the disulfide (II) or the compound (I) wherein $X^1$ is hydrogen.

Typical examples of the halogenating agent are chlorine gas, sulfuryl chloride, bromine, N-chlorosuccinimide and N-bromosuccinimide.

Examples of the solvent are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ketones such as acetone, methyl ethyl ketone, methyl isobutyl ketone, isophorone and cyclohexanone; fatty acids such as formic acid, acetic acid and oleic acid; alcohols such as methanol, ethanol, isopropanol, t-butanol, octanol, cyclohexanol, methyl cellosolve, diethylene glycol and glycerin; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, tdethylamine, N,N-diethylaniline, tributylamine and N-methylmorpholine; acid amides such as formamide, N,N-dimethylformamide and acetamide; and sulfur compounds such as dimethyl sulfoxide and sulfolane. These solvents can be used alone or in combination.

After completion of the reaction, the reaction mixture is subjected to an ordinary post-treatment such as organic solvent extraction and concentration. When sulfuryl chloride is used as the halogenating agent, a saturated aqueous solution of sodium hydrogen carbonate may be added to the reaction mixture, if necessary, before the organic solvent extraction and concentration. The reaction product may be purified, if necessary, by a purification procedure such as chromatography, distillation or recrystallization. Thus, the compound (I) can be obtained.

Typical examples of the compound (I) which can be prepared in this manner are shown in Table 1; these examples are, however, to be construed as merely illustrative, and not limitations of the present invention in any way whatsoever.

TABLE 1

| Compound No. | $X^1$ | $X^2$ | R |
|---|---|---|---|
| (1) | H | H | 2-$OCF_3$ |
| (2) | H | H | 3-$OCF_3$ |
| (3) | H | H | 4-$OCF_3$ |
| (4) | H | H | 2-$OCF_2H$ |
| (5) | H | H | 3-$OCF_2H$ |
| (6) | H | H | 4-$OCF_2H$ |
| (7) | H | H | 2-$OCF_2CF_2H$ |
| (8) | H | H | 3-$OCF_2CF_2H$ |
| (9) | H | H | 4-$OCF_2CF_2H$ |
| (10) | H | H | 4-$OCF_2Cl$ |
| (11) | Cl | Cl | 2-$OCF_3$ |
| (12) | Cl | Cl | 3-$OCF_3$ |
| (13) | Cl | Cl | 4-$OCF_3$ |
| (14) | Cl | Cl | 2-$OCF_2H$ |
| (15) | Cl | Cl | 3-$OCF_2H$ |
| (16) | Cl | Cl | 4-$OCF_2H$ |
| (17) | Cl | Cl | 2-$OCF_2CF_2H$ |
| (18) | Cl | Cl | 3-$OCF_2CF_2H$ |
| (19) | Cl | Cl | 4-$OCF_2CF_2H$ |
| (20) | Cl | Cl | 4-$OCF_2Cl$ |
| (21) | H | Cl | 2-$OCF_3$ |
| (22) | H | Cl | 3-$OCF_3$ |
| (23) | H | Cl | 4-$OCF_3$ |
| (24) | H | Cl | 2-$OCF_2H$ |
| (25) | H | Cl | 3-$OCF_2H$ |
| (26) | H | Cl | 4-$OCF_2H$ |
| (27) | H | Cl | 2-$OCF_2CF_2H$ |
| (28) | H | Cl | 3-$OCF_2CF_2H$ |
| (29) | H | Cl | 4-$OCF_2CF_2H$ |
| (30) | H | Cl | 4-$OCF_2Cl$ |
| (31) | Cl | H | 2-$OCF_3$ |
| (32) | Cl | H | 3-$OCF_3$ |
| (33) | Cl | H | 4-$OCF_3$ |
| (34) | Cl | H | 2-$OCF_2H$ |
| (35) | Cl | H | 3-$OCF_2H$ |
| (36) | Cl | H | 4-$OCF_2H$ |
| (37) | Cl | H | 2-$OCF_2CF_2H$ |
| (38) | Cl | H | 3-$OCF_2CF_2H$ |
| (39) | Cl | H | 4-$OCF_2CF_2H$ |
| (40) | Cl | H | 4-$OCF_2Cl$ |
| (41) | Br | Br | 2-$OCF_3$ |

TABLE 1-continued

![structure with X1, X2, N-S, carbonyl and aryl with R]

| Compound No. | X¹ | X² | R |
|---|---|---|---|
| (42) | Br | Br | 3-OCF$_3$ |
| (43) | Br | Br | 4-OCF$_3$ |
| (44) | Br | Br | 2-OCF$_2$H |
| (45) | Br | Br | 3-OCF$_2$H |
| (46) | Br | Br | 4-OCF$_2$H |
| (47) | Br | Br | 2-OCF$_2$CF$_2$H |
| (48) | Br | Br | 3-OCF$_2$CF$_2$H |
| (49) | Br | Br | 4-OCF$_2$CF$_2$H |
| (50) | Br | Br | 4-OCF$_2$Cl |

The disulfide (II) which is an intermediate compound for use in the production of the compound (I) can be prepared through the following pathway:

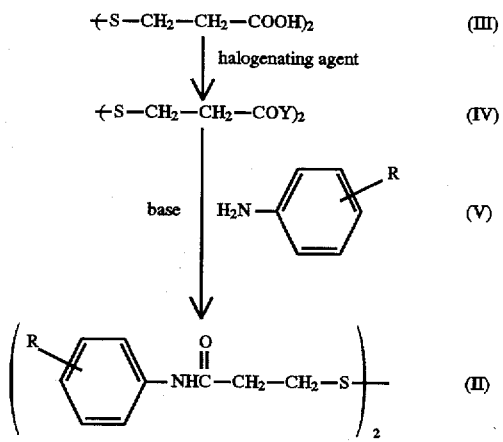

wherein Y is halogen and R is as defined above.

That is, 3,3'-dithiopropionic acid (III) is halogenated with a halogenating agent to give an acid halide (IV), which is then reacted with aniline derivative (V) in the presence of a base to give the desired disulfide (II).

The respective steps will hereinafter be explained in detail.

Step 1: Halogenation of 3,3'-dithiopropionic Acid (III) into Acid Halide (IV)

The reaction is usually carried out in a solvent and, if necessary, in the presence of a catalyst, at a temperature of 0° to 150° C. for a period of 0.5 to 20 hours. Examples of the halogenating agent are thionyl chloride, phosphorus pentachloride, phosphorus trichloride and phosgene. Examples of the catalyst are pyridine, triethylamine and N,N-dimethylformamide. The halogenating agent and catalyst are used in amounts of 2 to 5 equivalents and 0.05 to 0.25 equivalent, respectively, to one equivalent of 3,3'-dithiopropionic acid (III).

Step 2: Reaction of Acid Halide (IV) with Aniline Derivative (V) to Give Disulfide (II)

The reaction is usually carried out in a solvent and in the presence of a base at a temperature of 0° to 150° C. for a period of 1 to 24 hours. Examples of the base are inorganic bases such as sodium hydroxide, potassium hydroxide and potassium carbonate; and organic bases such as triethylamine and pyridine. The aniline derivative (V) and the base are used in amounts of 2 to 2.2 equivalents and 2 to 3 equivalents, respectively, to one equivalent of the acid halide (IV).

Typical examples of the solvent which can be used in steps 1 and 2 are aliphatic hydrocarbons such as hexane, heptane, ligroin and petroleum ether; aromatic hydrocarbons such as benzene, toluene and xylene; halogenated hydrocarbons such as chloroform, dichloroethane, chlorobenzene and dichlorobenzene; ethers such as diethyl ether, diisopropyl ether, dioxane, tetrahydrofuran and diethylene glycol dimethyl ether; esters such as ethyl formate, ethyl acetate, butyl acetate and diethyl carbonate; nitro compounds such as nitroethane and nitrobenzene; nitriles such as acetonitrile and isobutyronitrile; acid amides such as formamide, N,N-dimethylformamide and acetamide; and sulfur compounds such as dimethyl sulfoxide and sulfolane. These solvents can be used alone or in combination. In step 2, water may be added to the reaction system for double phase reaction.

After completion of the reaction in step 1, the reaction mixture is subjected to an ordinary post-treatment such as removal of the solvent. The acid halide (IV) may be isolated, if necessary, by distilling or purifying the reaction product. Alternatively, the reaction mixture obtained in step 1 may be used directly for the reaction in step 2.

After completion of the reaction in step 2, the reaction mixture is subjected to an ordinary post-treatment such as removal of the solvent, extraction with a solvent and concentration, followed by, if necessary, depositing crystals with the addition of aqueous hydrochloric acid and washing the crystals with water. The disulfide (II) may be isolated, if necessary, by purifying the reaction product by chromatography or recrystallization.

Typical examples of the disulfide (II) which can be prepared in this manner are shown in Table 2; these examples are, however, to be construed as merely illustrative, and not limitations of the present invention in any way whatsoever.

TABLE 2

| Compound No. | R |
|---|---|
| (101) | 2-OCF$_3$ |
| (102) | 3-OCF$_3$ |
| (103) | 4-OCF$_3$ |
| (104) | 2-OCF$_2$H |
| (105) | 3-OCF$_2$H |
| (106) | 4-OCF$_2$H |
| (107) | 2-OCF$_2$CF$_2$H |
| (108) | 3-OCF$_2$CF$_2$H |
| (109) | 4-OCF$_2$CF$_2$H |
| (110) | 4-OCF$_2$Cl |

The present invention will be further illustrated by the following examples, test examples, comparative examples and reference examples, which are not to be construed to limit the scope thereof. Unless otherwise indicated, the term "part(s)" refers to part(s) by weight. Specific examples of the compound (I) are designated by the respective compound numbers shown in Table 1.

Examples 1–4 and Comparative Examples 1–2

To each of the compound (3), (13) and (A) of the formula depicted below were added the ingredients as shown in Table 3. These mixtures were independently mixed and dispersed with a paint conditioner, which afforded paint compositions of Examples 1–4. In the same manner, paint compositions of Comparative Examples 1–2 were obtained. The trade names of the ingredients used are as follows:

LAROFLEX MP-45: vinyl chloride-vinyl isobutyl ether copolymer made by BASF A.G., in Germany PLIOLITE S-5B: styrene-butadiene copolymer made by The Goodyear Co., in the U.S.A.

AEROZIL #200: silica powder made by Degsa A.G., in Germany

The compound (A) used for comparison is represented by the formula:

TABLE 3

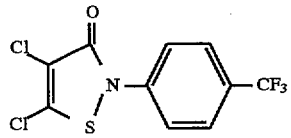

| Ingredients | Examples | | | | Comparative Examples | |
|---|---|---|---|---|---|---|
| | 1 | 2 | 3 | 4 | 1 | 2 |
| Compound (3) | 30 | 30 | | | | |
| Compound (13) | | | 30 | 15 | | |
| Compound (A) | | | | | 30 | |
| LAROFLEX MP-45 | 10 | | 10 | 10 | 10 | 10 |
| PLIOLITE S-5B | | 10 | | | | |
| Copper rhodanide | | | | | | 30 |
| Red iron oxide | 5 | 5 | 5 | 5 | 5 | 5 |
| Zinc oxide | 5 | 5 | 5 | 20 | 5 | 5 |
| AEROZIL #200 | 1 | 1 | 1 | 1 | 1 | 1 |
| Chlorinated paraffin | 2 | 2 | 2 | 2 | 2 | 2 |
| Rosin | 10 | 10 | 10 | 10 | 10 | 10 |
| Xylene | 32 | 32 | 32 | 32 | 32 | 32 |
| Methyl isobutyl ketone | 5 | 5 | 5 | 5 | 5 | 5 |
| Total | 100 | 100 | 100 | 100 | 100 | 100 |

Test Example 1

Each of the paint compositions obtained in Examples 1–4 and Comparative Examples 1–2 was applied by means of an air spray to a sandblasted steel panel of 300×100×3.2 mm in size, which had been coated with a shop primer and an anti-corrosive paint of the vinyl tar type, in such a manner that a dry film of 100 μm in thickness was obtained. These sample panels were dried for 7 days, and immersed and left at rest in the sea off the coast of Miyajima in the Bay of Hiroshima at Hiroshima Prefecture, and examined for the adhesion of harmful aquatic animals and plants as well as the adhesion of slime. The results are shown in Table 4. The amount of adhering harmful aquatic animals and plants in the table was evaluated as the percentage (%) of area to which they adhered, and the amount of adhering slime in the table was evaluated by the following criteria:

0: no adhesion; 1: slight adhesion; 2: small adhesion; 3: moderate adhesion; 4: moderate to great adhesion; and 5: geat adhesion.

TABLE 4

| | Immersion period | | | | | |
|---|---|---|---|---|---|---|
| | 6 months | | 12 months | | 18 months | |
| Adhering organisms | Slime | Harmful aquatic animals and plants | Slime | Harmful aquatic animals and plants | Slime | Harmful aquatic animals and plants |
| Example 1 | 1 | 0 | 1 | 5 | 2 | 10 |
| Example 2 | 2 | 0 | 2 | 5 | 3 | 15 |
| Example 3 | 0 | 0 | 1 | 0 | 1 | 0 |
| Example 4 | 1 | 0 | 2 | 10 | 3 | 30 |
| Comparative Example 1 | 4 | 30 | 5 | 90 | 5 | 100 |
| Comparative Example 2 | 5 | 10 | 5 | 60 | 5 | 100 |

Examples 5–9 and Comparative Examples 3–5

Using compound (3), (13) or (A) and other ingredients as shown in Table 5, five paint compositions of Examples 5–9 and three paint compositions of Comparative Examples 3–5 were obtained in the same manner as described in Examples 1–4.

TABLE 5

| Ingredients | Examples | | | | | Comparative Examples | | |
|---|---|---|---|---|---|---|---|---|
| | 5 | 6 | 7 | 8 | 9 | 3 | 4 | 5 |
| Compound (3) | 5 | | | 5 | | | | |
| Compound (13) | | 5 | 5 | | 5 | | | |
| Compound (A) | | | | | | 5 | | |
| LAROFLEX MP-45 | 10 | 10 | | 10 | | 10 | | 10 |
| PLIOLITE S-5B | | | 10 | | 10 | | 10 | |
| Cuprous oxide | 35 | 35 | 35 | 20 | 20 | 35 | 35 | |
| Copper rhodanide | | | | | | | | 20 |
| Zinc dimethyldithio-carbamate | | | | | 10 | | | |
| N,N-dimethyl-N'-(3,4-di-chloro-phenyl)urea | | | | 10 | | | | |
| 2-Pyridinethiol-1-oxide zinc salt | | | | | | | | 10 |
| Red iron oxide | 5 | 5 | 5 | 5 | 5 | 5 | 5 | 5 |
| Zinc oxide | 5 | 5 | 5 | 5 | 5 | 5 | 5 | 5 |
| AEROZIL #200 | 1 | 1 | 1 | 1 | 1 | 1 | 1 | 1 |
| Chlorinated paraffin | 2 | 2 | 2 | 2 | 2 | 2 | 2 | 2 |
| Rosin | 10 | 10 | 10 | 10 | 10 | 10 | 10 | 10 |
| Xylene | 22 | 22 | 22 | 27 | 27 | 22 | 27 | 32 |
| Methyl isobutyl ketone | 5 | 5 | 5 | 5 | 5 | 5 | 5 | 5 |
| Total | 100 | 100 | 100 | 100 | 100 | 100 | 100 | 100 |

Test Example 2

The paint compositions obtained in Examples 5–9 and Comparative Examples 3–5 were examined by the same method as used in Test Example 1. The results are shown in Table 6.

TABLE 6

| Adhering organisms | Immersion period | | | | | |
|---|---|---|---|---|---|---|
| | 6 months | | 12 months | | 18 months | |
| | Slime | Harmful aquatic animals and plants | Slime | Harmful aquatic animals and plants | Slime | Harmful aquatic animals and plants |
| Example 5 | 1 | 0 | 2 | 0 | 2 | 0 |
| Example 6 | 0 | 0 | 1 | 0 | 1 | 0 |
| Example 7 | 1 | 0 | 1 | 0 | 2 | 0 |
| Example 8 | 2 | 0 | 2 | 0 | 3 | 20 |
| Example 9 | 1 | 0 | 2 | 0 | 2 | 10 |
| Comparative Example 3 | 5 | 0 | 5 | 15 | 5 | 40 |
| Comparative Example 4 | 5 | 0 | 5 | 10 | 5 | 30 |
| Comparative Example 5 | 3 | 0 | 5 | 40 | 5 | 80 |

Reference Example 1: Preparation of Compounds (3) and (23)

First, 18.73 g of N,N'-di-(4-trifluoromethoxyphenyl)-3,3'-dithiopropionamide was suspended in 200 ml of toluene, after which 23.92 g of sulfuryl chloride was then added dropwise to the suspension at room temperature, and the resultant mixture was stirred for 12 hours. After completion of the reaction, the reaction mixture was concentrated, and 250 ml of a saturated aqueous solution of sodium hydrogencarbonate was added to the concentrate with taking care to prevent foaming. The product was extracted with ethyl acetate. The organic layer was washed with water, dried with magnesium sulfate, and concentrated. The concentrate was purified by column chromatography (hexane: ethyl acetate= 3:1 to 1:1) to give 6.4 g of 2-(4-trifluoromethoxyphenyl)-4-isothiazolin-3-on (compound (3); m.p., 117°–118° C.) and 5.1 g of 2-(4-trifluoromethoxyphenyl)-5-chloro-4-isothiazolin-3-on (compound (23); m.p., 51°–52° C.).

Reference Example 2: Preparation of Compound (13)

First, a mixture containing 6.4 g of 2-(4-trifluoromethoxyphenyl)-4-isothiazolin-3-on and 5.1 g of 2-(4-trifluoromethoxyphenyl)-5-chloro-4-isothiazolin-3-on was suspended in 100 ml of dichloromethane, after which 19 g of sulfuryl chloride was then added dropwise to the suspension at room temperature, and the resultant mixture was stirred for 12 hours. After completion of the reaction, 200 ml of a saturated aqueous solution of sodium hydrogencarbonate was added to the reaction mixture, and the dichloromethane layer was separated. The aqueous layer was extracted with 150 ml of dichloromethane. The combined dichloromethane layer was washed with water, dried with magnesium sulfate, and concentrated. The concentrate was purified by column chromatography (hexane:ethyl acetate=6:1) to give 4 g of 2-(4-trifluoromethoxyphenyl)-4,5-dichloro-4-isothiazolin-3-on (compound (13); m.p., 129°–130° C.).

Reference Example 3: Preparation of Compound (103)

First, a mixture containing 100 g of p-trifluoromethoxyaniline, 700 ml of toluene and 98.2 g of pyridine was cooled to 0° C., after which 69.7 g of 3,3'-dithiopropionic acid dichloride were added dropwise to the mixture, and the resultant mixture was stirred at room temperature (approximately 20° C.) for 1 hour and then at 80° C. for 2 hours. After completion of the reaction, the solvent was removed from the reaction mixture, and 500 ml of a 5% aqueous solution of hydrochloric acid was added to the residue for crystallization, and the deposited crystals were collected by filtration. The crystals were washed with water and dried under reduced pressure to give 160.3 g of N,N'-di(4-trifluoromethoxyphenyl)-3,3'-dithiopropionamide.

$^1$H-NMR (CDCl$_3$-DMSO-d$^6$)δ(ppm): 10.3 (brs, 2H), 7.7 (d, 4H), 7.1 (d, 4H), 2.9 (m, 8H)

IR (KBr): 3310 cm$^{-1}$, 1661 cm$^{-1}$

Reference Example 4: Preparation of 3,3'-dithiopropionic Acid Dichloride

First, 100 g of 3,3'-dithiopropionic acid was added to 500 ml of toluene, after which 2.5 ml of N,N-dimethylformamide was added to the mixture and 135.5 g of thionyl chloride was then added dropwise to the mixture, the resultant mixture was stirred at 50° C. for 2 hours. After completion of the reaction, the toluene was removed from the reaction mixture, which gave 122 g of 3,3'-dithiopropionic acid dichloride as a brown liquid.

$^1$H-NMR (CDCl$_3$)δ(ppm): 3.3 (t, 4H), 3.0 (t, 4H)

IR (neat): 1800 cm$^{-1}$

What is claimed is:

1. A controlling agent composition against harmful aquatic organisms, which comprises (a) an N-phenylisothiazolone derivative of the formula (I):

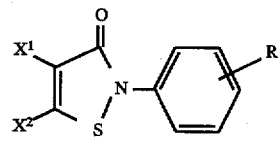

wherein X$^1$ and X$^2$ are the same or different and are independently hydrogen, chlorine or bromine; and R is haloalkoxy and (b) a copper compound or a metallic copper.

2. A controlling agent composition according to claim 1, wherein the copper compound is selected from the group consisting of cuprous oxide, copper rhodanide, oxine-copper, copper naphthenate, copper glycinate, cuprous chloride and cuprous carbonate.

3. A controlling agent composition according to claim 2, wherein the copper compound is cuprous oxide.

4. An antifouling composition which is effective against harmful aquatic organisms, which comprises an effective amount of N-phenylisothiazolone derivative of the formula:

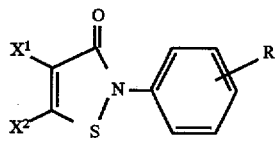

wherein X$^1$ and X$^2$ are the same or different and are independently hydrogen, chlorine or bromine; and R is C1–C8 haloalkoxy, and a resin.

5. An antifouling composition according to claim 4, which further comprises a copper compound or a metallic copper.

6. An antifouling composition according to claim 4, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

7. A method for preventing or inhibiting the adhesion of harmful aquatic organisms to a water-exposed article, which comprises applying an effective amount of an antifouling composition of claim 4 to the water-exposed article.

8. A method according to claim 7, wherein the water-exposed article is a marine vessel.

9. An antifouling composition according to claim 4, wherein the amount of N-phenylisothiazolone derivative is 0.1% to 60% by weight and the amount of resin is 0.1% to 80% by weight, both of which is based on the total weight of the composition.

10. An antifouling composition according to claim 5, wherein the amount of N-phenylisothiazolone derivative is 0.1% to 60% by weight and the amount of resin is 0.1% to 80% by weight, both of which is based on the total weight of the composition, and the amount of copper compound or metallic copper is 0.1 to 100 parts by weight to one part by weight of N-phenylisothiazolone derivative, provided that the total amount of N-phenylisothiazolone derivative and copper compound or metallic copper is 0.1% to 80% by weight, based on the total weight of the composition.

11. An antifouling composition according to claim 5, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

12. An antifouling composition which is effective against harmful aquatic organisms, which comprises an N-phenylisothiazolone derivative of the formula:

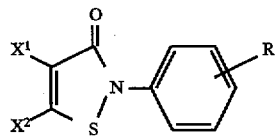

(I)

wherein $X^1$ and $X^2$ are the same or different and are independently hydrogen, chlorine or bromine; and R is C1–C8 fluoroalkoxy, and a resin.

13. An antifouling composition according to claim 12, wherein the amount of N-phenylisothiazolone derivative is 0.1% to 60% by weight and the amount of resin is 0.1% to 80% by weight, both of which is based on the total weight of the composition.

14. An antifouling composition according to claim 12, which further comprises a copper compound or a metallic copper.

15. An antifouling composition according to claim 14, wherein the amount of N-phenylisothiazolone derivative is 0.1% to 60% by weight and the amount of resin is 0.1% to 80% by weight, both of which is based on the total weight of the composition, and the amount of copper compound or metallic copper is 0.1 to 100 parts by weight to one part by weight of N-phenylisothiazolone derivative and copper compound or metallic copper is 0.1% to 80% by weight, based on the total weight of the composition.

16. An antifouling composition according to claim 12, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

17. An antifouling composition according to claim 12, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

18. An antifouling composition according to claim 14, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

19. An antifouling composition according to claim 15, wherein the resin is selected from the group consisting of vinyl chloride resins, vinyl chloride-vinyl acetate copolymers, vinyl chloride-vinyl isobutyl ether copolymers, chlorinated rubber resins, chlorinated polyethylene resins, chlorinated polypropylene resins, acrylic resins, styrene-butadiene copolymers, polyester resins, epoxy resins, phenolic resins, synthetic rubbers, silicone rubbers, silicone resins, petroleum resins, oil resins, rosin ester resins, rosin soap and rosin.

20. A method for preventing or inhibiting the adhesion of harmful aquatic organisms to a water-exposed article, which comprises applying an effective amount of an antifouling composition according to claim 12 to the water-exposed article.

21. A method according to claim 20, wherein the water-exposed article is a marine vessel.

22. A method for preventing or inhibiting the adhesion of harmful aquatic organisms to a water-exposed article, which comprises applying an effective amount of an antifouling composition according to claim 2 to the water-exposed article.

23. A method according to claim 22, wherein the water-exposed article is a marine vessel.

* * * * *